United States Patent
Peckham

(10) Patent No.: US 7,806,911 B2
(45) Date of Patent: Oct. 5, 2010

(54) FIXATION PLATE AND METHOD OF USE

(75) Inventor: Steven M. Peckham, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 731 days.

(21) Appl. No.: 11/404,305

(22) Filed: Apr. 14, 2006

(65) Prior Publication Data
US 2007/0270812 A1 Nov. 22, 2007

(51) Int. Cl.
A61B 17/70 (2006.01)
A61B 17/80 (2006.01)

(52) U.S. Cl. ............ 606/248; 606/70; 606/71; 606/285; 606/297; 606/249; 606/298

(58) Field of Classification Search ... 623/17.11–17.16; 606/248, 249, 70, 712, 283–285, 297–299
See application file for complete search history.

(56) References Cited

U.S. PATENT DOCUMENTS

| | | | |
|---|---|---|---|
| 3,648,691 A * | 3/1972 | Lumb et al. | 606/279 |
| 6,312,431 B1 | 11/2001 | Asfora | |
| 6,364,883 B1 * | 4/2002 | Santilli | 606/279 |
| 6,635,087 B2 | 10/2003 | Angelucci et al. | |
| 6,692,498 B1 | 2/2004 | Niiranen et al. | |
| 6,978,166 B2 | 12/2005 | Foley et al. | |
| 2003/0040746 A1 * | 2/2003 | Mitchell et al. | 606/61 |
| 2004/0030388 A1 * | 2/2004 | Null et al. | 623/17.11 |
| 2006/0106381 A1 * | 5/2006 | Ferree et al. | 606/61 |

FOREIGN PATENT DOCUMENTS

| WO | 2004021905 A1 | 3/2004 |
|---|---|---|
| WO | WO 2004/021905 A1 * | 3/2004 |
| WO | 2006116853 A1 | 11/2006 |

OTHER PUBLICATIONS

International Search Report PCT/US2007/065591.

* cited by examiner

Primary Examiner—Eduardo C Robert
Assistant Examiner—Julianna N Harvey

(57) ABSTRACT

A spinous process clamp employs a pair of elongate plates that are positioned on either side of the spinous processes of vertebrae that are to be fused. The plates are joined by fasteners, preferably bolts and nuts. The plates include a recess on the bone facing side of the plate for retaining a bone growth promoting substance. When the bolts and nuts are tightened, the spinous processes are clamped between the plates, thereby pressing the bone growth promoting substance against the bone and encouraging bone growth across the vertebrae fixed by the plates.

19 Claims, 3 Drawing Sheets

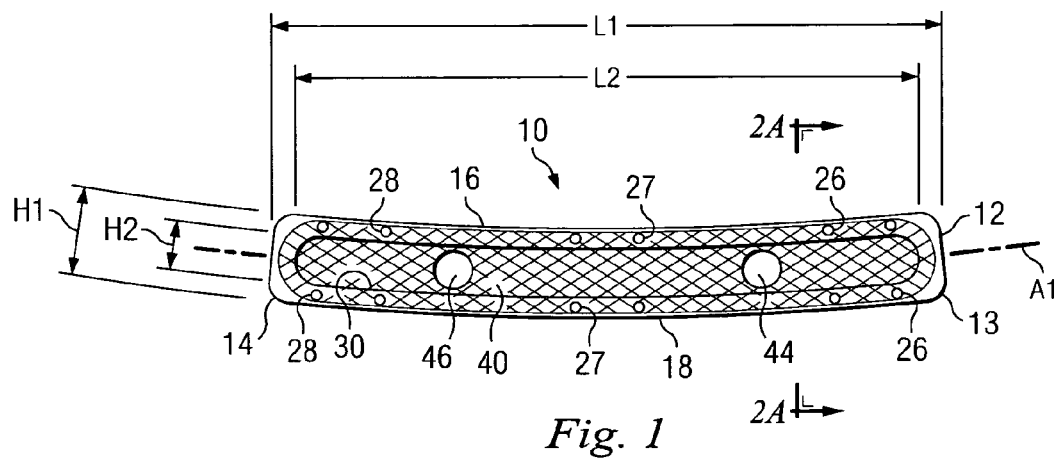
Fig. 1
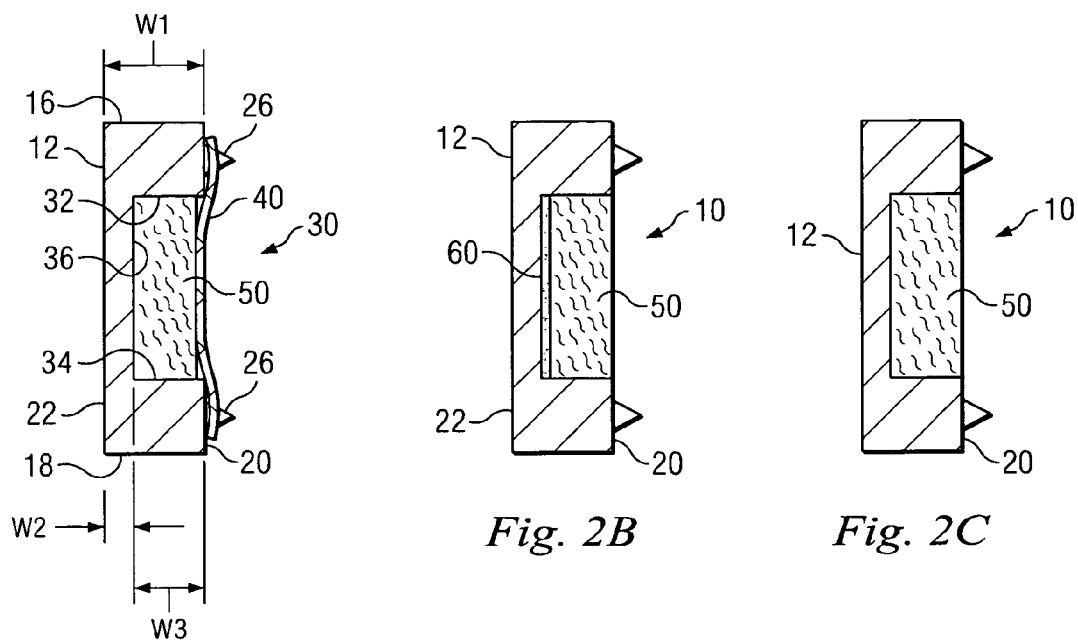
Fig. 2A
Fig. 2B
Fig. 2C

FIXATION PLATE AND METHOD OF USE

BACKGROUND

The present application relates generally to a fixation system for the treatment of the skeletal system. More particularly, the present invention may be applied to treatment of the human spine.

Spinal fusion is performed to prevent motion between mobile segments of the spine. A variety of reasons exist for performing spinal fusion. The spine may be unstable due to a traumatic injury, surgery, or invasion and destruction of the vertebrae by tumor. Continued motion of particular segments of the spine may cause overgrowth of joint and ligamentous tissue which, in turn, may compress the spinal cord or its nerves. The curvature of the spine may become abnormal and cause deformity or neurological problems. In these instances, it may be desirable to prevent spinal motion at the affected levels.

The spine is composed of individual bones, or vertebrae, stacked on top of each other in a column. Each vertebra includes a cylindrical vertebral body, which participates in weight bearing, and an arch of bone (comprising the lamina and spinous process) which protects the spinal cord and its coverings. The bony arch is connected to the vertebral body by two small columns of bone, referred to as the pedicles. The circular canal between the body, the arch, and the pedicles houses the spinal cord and is called the spinal canal. Between adjacent vertebral bodies lie the intervertebral discs. These are cartilaginous structures that function as shock absorbers for the spine. Facet joints connect the bony arches of the spine and permit spinal motion between adjacent vertebrae.

Spinal instrumentation is employed as an adjunct to successful spinal fusion. The instrumentation immobilizes the spine while the body forms new, solid bone. Spinal fusion usually is performed by surgically exposing the area of the spine to be fused and thereafter preparing the exposed bone by removing soft tissue and ligaments so new bone can form over the area. After the surgical site has been prepared, an autogenic bone graft (from another part of the body, usually the hip) or an allogenic bone graft (from a cadaver) can be implanted in the prepared area so that new bone can form around and within the implant. Implants have been developed in an attempt to avoid the problems associated with acquiring a bone graft implant. Regardless of the type of implant that is used, the chances of achieving a successful fusion are enhanced if motion in the area is minimized or prevented while new bone forms.

Although there have been advances in this area, there remains a need for improved stabilization systems for use in skeletal fixation and boney fusion procedures.

SUMMARY OF THE INVENTION

The present application relates generally to fixation of the skeletal system.

In one embodiment, a skeletal fixation plate is provided comprising an elongated plate having a bone growth promoting substance on one side and a retention layer joined to the plate to hold the bone growth promoting substance to the plate. In a further aspect, the retention layer is a porous material.

In yet a further aspect, the present invention provides a fixation plate for joining at least two vertebrae. The fixation plate includes a retention channel recessed into a bone engaging surface of the plate. In one aspect, the retention channel has a depth that is greater than one half of the thickness of the plate.

In another embodiment, the present invention provides a method for treating at least two vertebrae, comprising providing a fixation plate with a retention channel formed a bone engaging side, and placing a bone growth promoting material in the channel. The fixation plate is positioned in the patient adjacent the vertebrae to be fused with the retention channel facing the bone and the plate is fixed to the bone.

Further aspects, forms, embodiments, objects, features, benefits, and advantages of the present invention shall become apparent from the detailed drawings and descriptions provided herein.

BRIEF DESCRIPTION OF THE DRAWINGS

FIG. 1 is a side view of a fixation plate system according to one aspect of the present invention.

FIG. 2A is a cross-sectional view taken along line 2A-2A of FIG. 1.

FIGS. 2B and 2C are cross-sectional views of alternative embodiments similar to the fixation plate of FIG. 1.

DETAILED DESCRIPTION OF THE ILLUSTRATED EMBODIMENTS

Figure 3:
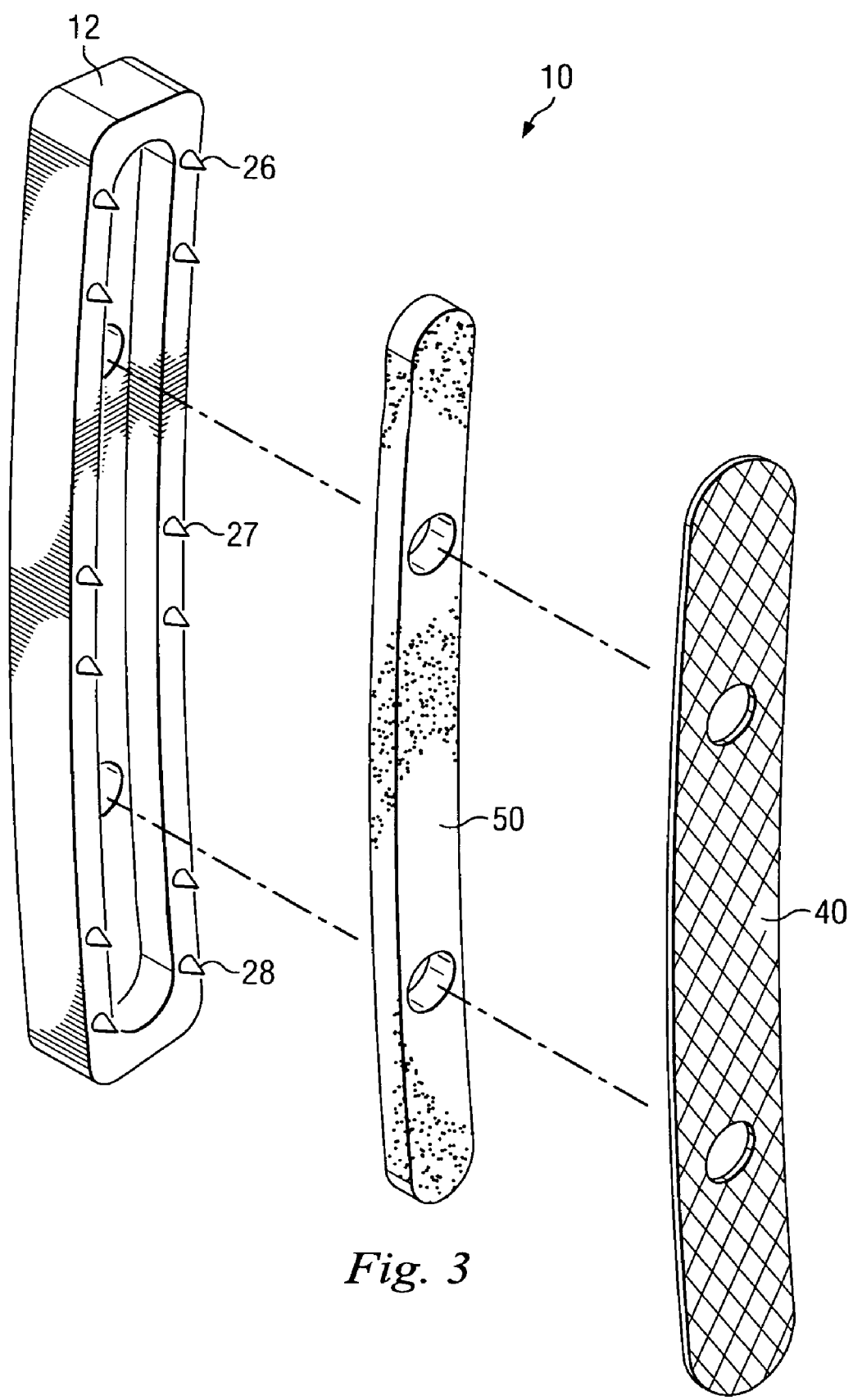
FIG. 3 is a partially exploded top view of the fixation plate system shown in FIG. 1.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring now to FIGS. 1 and 2A, there is shown an embodiment of a fixation plate system 10 according to the present invention. The fixation plate system 10 includes an elongated plate 12 extending from first end 13 to opposite second end 14 along longitudinal axis A1. The plate 12 has a length L1 extending between first end 13 and second end 14, and is illustrated with a slight curve to substantially match the curvature of the lumbar spine. The plate 12 has a top surface 16 and an opposite bottom surface 18. The plate 12 has a height H1 extending between the top surface 16 and the bottom surface 18. The plate 12 illustrated in FIG. 2A has a medial bone facing side 20 and an opposite lateral facing side 22 with a thickness or width W1 extending therebetween. On the bone facing surface 20 there are a series of bone engaging spikes 26, 27 and 28 adapted fixedly engage bone by at least partially penetrating the surface of the bone. A pair of fastener receiving holes 44 and 46 extend through the plate 12.

The fixation plate system 10 according to the illustrated embodiment includes a retention channel 30 recessed within the bone facing side 20. As shown in FIG. 1, the retention channel 30 extends along the longitudinal axis A1 for a length L2 between first end and the opposite second end of the retention channel. As shown in FIG. 2A, the retention channel 30 is defined by upper surface 32, lower surface 34 and lateral surface 36. The retention channel 30 has a thickness or depth of W3 while the remaining portion of the plate laterally adjacent the retention channel has a thickness or depth W2. In the illustrated embodiment, the depth W3 of the retention channel is greater than one half the thickness W1 of the plate 12 such that W3 is greater than W2. The retention channel 30 has a height H2 extending between upper surface 32 and lower surface 34. In the illustrated embodiment, the height H2 is equal to approximately 50% of the plate height H1.

Disposed within the retention channel 30 is a bone growth promoting substance 50. In the illustrated embodiment, the bone growth promoting substance has been formed to substantially match the contours of the retention channel 30. The bone growth promoting substance is provided to interact with the native or grafted bone in the spinal column to cooperate in the formation of a boney fusion or fixation. The bone growth promoting material is held in position by the placement of a retention member 40 across the medial opening of the retention channel into the bone face 20 of the plate 12. In the illustrated embodiment, the retention member 40 extends from upper wall 32 to lower wall 34 and along the length L2 of the retention channel 30. The retention member 40 is a mesh structure allowing contact of bodily fluids and other cells with the bone growth promoting substance. In a preferred aspect, the retention member mesh 40 has a pore size that is large enough to encourage bone growth across the mesh. Further, in another aspect, the hole size in the mesh 40 is greater than 50% of the total area. In this embodiment, the bone growth promoting substance is a least partially malleable and a portion of the bone growth promoting substance may extend through the openings in the mesh to contact the native or grafted bone positioned in the spine. In this embodiment, the mesh is at least partially embedded into the bone growth promoting substance.

In one embodiment the retention member is a metal or synthetic material adapted to be encased in the bone as it forms. In another embodiment, the retention member is a resorbable material configured to resorb over time as the bone grows. In still a further embodiment, the retention member is a membrane having small pore sizes. In one aspect, the membrane has pores sizes larger than 50 microns. In another aspect, the pore sizes range from 50 microns to 1,000 microns. In a further aspect, the membrane is at least in part resorbable such that over time the pores enlarge as the bone begins to form. Still further, in the embodiment utilizing a membrane layer to retain the bone growth promoting substance in the retention channel, the substance may be a substantially liquid or slurry material that is injected via a needle or cannula through the membrane previously attached to the plate and into the retention channel. In this embodiment, the plate and the membrane may be preassembled prior to delivery to the surgeon. Moreover, the membrane may act to slowly release the bone growth material into the patient's system adjacent the fusion site over a period of days, weeks or months depending on the healing rate desired.

In an alternative embodiment illustrated in FIG. 2B, plate 2 is provided with a retention channel 30 as previously described with respect to the embodiment of FIGS. 1 and 2A. In the embodiment of FIG. 2B, the bone growth promoting substance 50 is positioned in the retention channel 30 such that it has a medial surface in substantial alignment with the medial bone facing surface of plate 12. In this embodiment, the bone growth promoting substance 50 is substantially rigid and is retained in the retention channel by a medical grade adhesive layer 60 suitable for human implantation. Suitable adhesives may include, but without limitation to alternative adhesives, fibrin glue or bone cement. While adhesive layer 60 is shown on the lateral wall of the retention channel 30, it is contemplated that the adhesive may alternatively or additionally be placed on the upper or lower surfaces of the retention channel.

In a further alternative embodiment shown in FIG. 2C, there is shown a plate 12 with a retention channel as previously described with respect to FIGS. 1 and 2A. In the illustrated embodiment, bone growth promoting substance 50 has been configured to be form fitting within the retention channel such that the substance 50 is retained in position by direct engagement with the walls of the retention channel. In one form, the bone growth promoting substance is rigid and is press fit into the retention channel. In another form, the bone growth promoting substance is a substantially flowable material. The retention channel is filled with the material and the material is either allowed to set to a more solid condition or the material is compressed to a more solid form.

It is contemplated that plate 12 is formed of a substantially rigid material. In one embodiment the plate is formed of a metallic material such as medical grade stainless steel, titanium, or cobalt chrome. In another form, the plate is formed of a synthetic material such as plastic, polymer, PEEK, ceramic, carbon fiber reinforced polymer, etc. Further, in one embodiment the plate is constructed to substantially rigid and to inhibit all movement along its length. In another form, the plate is constructed to allow at least partial movement or flexion such that the bone experiences movement between the adjacent vertebrae. These materials are disclosed without limitation to use of other materials to form the plate of the present invention.

As used herein, a "bone growth promoting substance" includes but is not limited to a "biologically active component", with or without a "biomaterial carrier."

A "biologically active component" includes but is not limited to, autograft bone, allograft bone, xenograft bone, autogenic chondrocytes with retroviral viral vector or plasmid viral vector; allogenic chondrocytes with retroviral viral vector or plasmid viral vector; and fibroblasts. The acronym "LIM" is derived from the three genes in which the LIM domain was first described. The LIM domain is a cysteine-rich motif defined by 50-60 amino acids with the consensus sequence CX2CX16-23HX2CX2CX2CX16-21CX2(C/H/D), which contains two closely associated zinc-binding modules. LIM mineralization proteins include but are not limited to those described in U.S. Patent Application Publication No. 2003/0180266 A1, the disclosure of which is incorporated herein by reference. "Growth factors" include but are not limited to transforming growth factor (TGF)-beta 1, TGF-beta 2, TGF-beta 3, bone morphogenetic protein (BMP)-2, BMP-3, BMP-4, BMP-6, BMP-7, BMP-9, fibroblast growth factor (FGF), growth and differentiation factor (for example, GDF 5)platelet derived growth factor (PDGF), insulin-like growth factor (ILGF); human endothelial cell growth factor (ECGF); epidermal growth factor (EGF); nerve growth factor (NGF); and vascular endothelial growth factor (VEGF). "Anti-IL-1" components include but are not limited to those described in U.S. Patent Application Publication Nos. 2003/0220283 and 2005/0260159, the entire disclosures of which are incorporated herein by reference. "Stem cell material" includes but is not limited to dedifferentiated stem cells, undifferentiated stem cells, and mesenchymal stem cells. "Stem cell material" also includes but is not limited to stem cells extracted from marrow, which may include lipo-derived stem cell material, and adipose-derived stem cell material, such as described in U.S. Publication Nos. 2004/0193274 and 2005/0118228, each of which is incorporated herein by reference. "Stem cell material" also includes but is not limited to stem cells derived from adipose tissue as described in U.S. Patent Application Publication Nos. 2003/0161816, 2004/0097867 and 2004/0106196, each of which is incorporated herein by reference.

A "biologically active component" also includes but is not limited to an engineered cell comprising a nucleic acid for encoding a protein or variant thereof, such as a BMP, a LIM mineralization protein, or an SMAD protein as described in U.S. Patent Application Publication Nos. 2003/0219423 and 2003/0228292, the entire disclosures of which are incorporated herein by reference; and a recombinant human bone morphogenetic protein, such as described in U.S. Patent Application Publication No. 2004/0024081, the entire disclosure of which is incorporated herein by reference.

As used herein, "biomaterial carriers" include but are not limited to the following, either alone or in combination, autograft bone, allograft bone, xenograft bone, demineralized bone matrix, collagen, gelatin, hyaluronic acid, fibrin, albumin, keratin, silk, elastin, calcium phosphates (for example hydroxyapatite and tricalcium phosphate),glycosaminoglycans (GAGs), polyethylene glycol (PEG), polyethylene oxide (PEO), polyvinyl alcohol (PVA) hydrogel, polyvinyl pyrrolidone (PVP), co-polymers of PVA and PVP, other polysaccharides, platelet gel, peptides, carboxymethyl cellulose, and other modified starches and celluloses. Collagen includes but is not limited to collagen-based material, which may be autogenic, allogenic, xenogenic or of human-recombinant origin, such as the collagen-based material described in U.S. Patent Application Publication Nos. 2004/0054414 and 2004/0228901, the entire disclosures of which are incorporated herein by reference.

For example, but without limitation the bone growth promoting substance can take the form of a solution, a suspension, emulsion, paste, a putty, a particulate material, a fibrous material, a plug, a solid, porous, woven or non-woven material, or in a dehydrated or rehydrated state.

Figure 4:
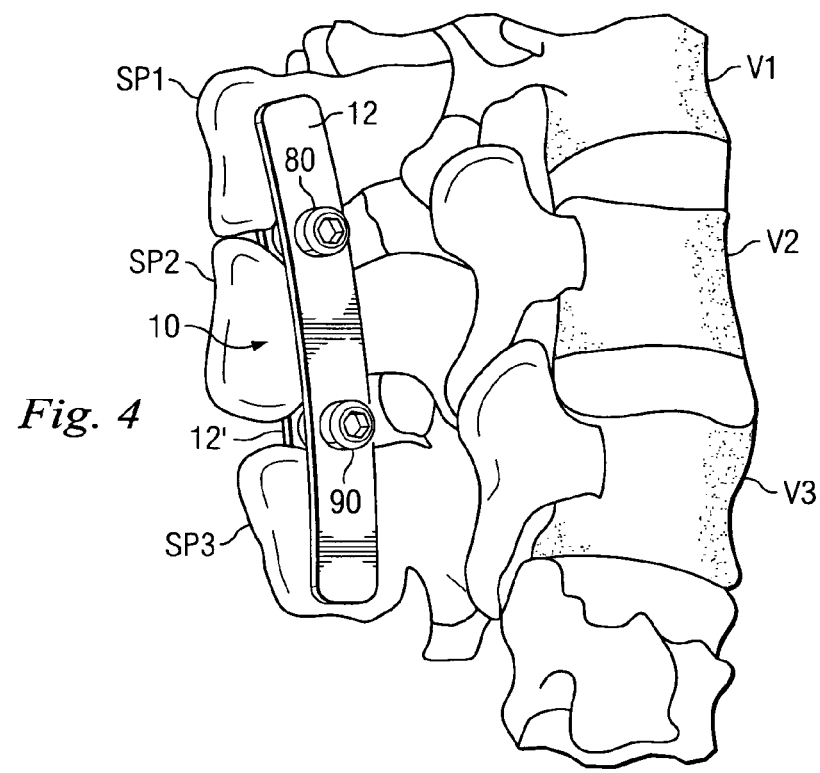
FIG. 4 is a partial perspective side view of the spine with a fixation system according to another aspect of the present invention.
Figure 5:
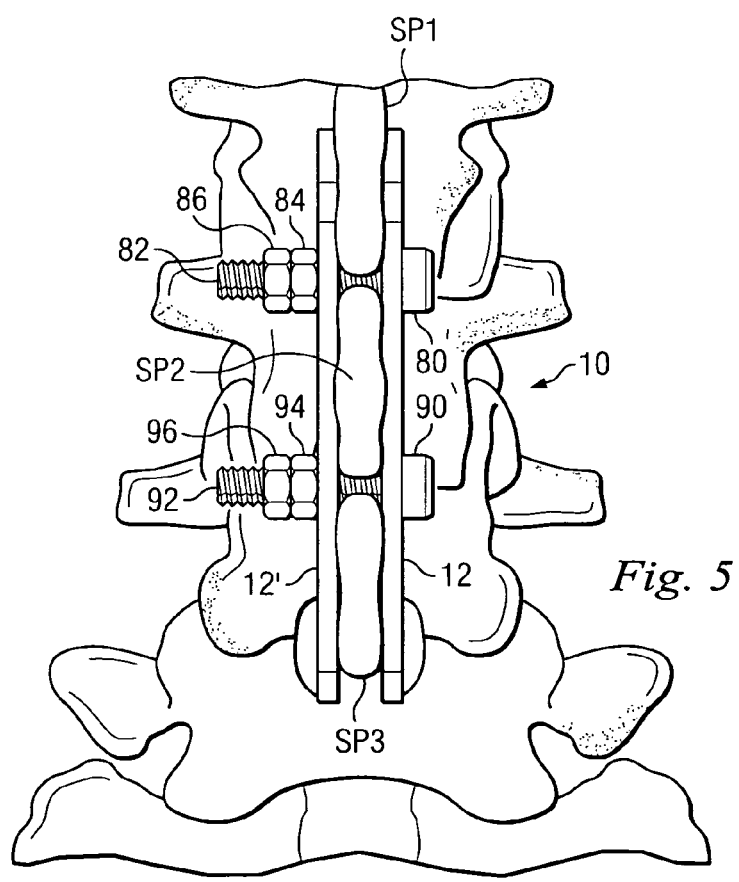
FIG. 5 is a rear view of the spine with the fixation system of the FIG. 4.

Referring now to FIGS. 3-5, use of the fixation system 10 according to the present invention is illustrated. In FIG. 3, there is shown a plate 12, a bone growth promoting substance 50 and a retention member 40. In one aspect, all of the these components are provided preassembled in a single use kit. In another aspect, the plate 12 and retention member 40 are provided in a kit. The bone growth promoting substance is obtained separately from a manufactured source, a bone bank or from a graft site on the patient. The bone growth promoting substance 50 is aligned with the retention channel of the plate 12. The substance 50 is inserted into the channel. Retention member 40 is aligned with the plate to extend over at least a portion of the retention channel and then affixed to the plate. In one form, the retention member 40 extends over spikes 26, 27 and 28 to maintain its position. In another alternative embodiment, the mesh includes one or more retaining clips (not shown) that engage a portion of an annular recess (not shown) formed within the retention channel. In another form, the retention member 40 is adhered to the plate with a biocompatible adhesive.

Once the plate 12, bone growth promoting substance 50 and retention member 40 are assembled, they may be applied to the body. In the use illustrated in FIGS. 4 and 5, the fixation plate system 10 according to the present invention is applied to the human spine across the spinous processes SP1, SP2, and SP3 of vertebrae V1, V2 and V3, respectively. Although the current procedure is described with respect to fixation of three vertebrae, the current invention is also applicable to two or more than three vertebrae. Further, while a spinous process fusion is shown for the purpose of illustration, it is contemplated that a plate configured as described above may be applied singly or together with other fixation plates to all type of bone fusion procedures. In the illustrated embodiment, a plate 12 is prepared as described above with respect to FIG. 3. Additionally, a corresponding plate 12' for the opposite side of the spinous processes is also prepared in accordance with the present invention. Surgical access is gained to extend along both sides of the spinous processes SP1, SP2, and SP3. Plate 12 is inserted into the patient and positioned adjacent the spinous processes with the retention channel orient toward the bone. Plate 12' is inserted into the patient and positioned adjacent to the spinous processes opposite plate 12 with the retention channel oriented toward the bone. The threaded post 82 of bolt 80 is passed through opening 44 of plate 12 and a similar opening in plate 12'. A first nut 84 is threaded on to post 82 and urged to force plate 12' toward plate 12 such that the spike will extend into and engage the bone. A locking nut 82 is advanced on the threaded post 82 to prevent nut 84 from loosening. In a similar fashion, threaded post 92 of bolt 90 is passed through opening 46 of plate 12 and a corresponding opening in plate 12'. A nut 94 is advanced on the threaded post to urge the plates toward each other and the locking nut is advanced to lock the first nut 94 in position.

In the illustrated embodiment, fasteners 80 and 90 extend through apertures 44 and 46, respectively. The fastener 80 extends through the space between SP1 and SP2, while fastener 90 extends through the space between SP2 and SP3. It is contemplated that the holes in the plate may be moved so the fasteners extend outside of the area where the boney fusion is intended to occur. For example, in one embodiment, the plate have a length extending beyond the spinous process to be fused and the openings in the plates are positioned superior and interior of the impacted spinous process. The fasteners extend through the openings outside of the fusion zone to secure the plates to the bone and not interfere with the fusion process. In another embodiment, the plates are substantially solid without any openings for the fasteners 80 and 90. In this embodiment, a pair of U-shaped clips extending over the lateral side of each plate 12 and 12' replace fasteners 80 and 90 to hold the plates in position with respect to the bone. The clips can be unitary spring biased members or can be clamps that can be mechanical adjusted to urge plates 12 and 12' towards each other.

Although spikes 26, 27 and 28 have been shown as the bone engaging surface on the bone facing side of the plate 12 for the purpose of illustration, it is contemplated that the bone engaging surface can have knurling, roughening, sintered material, teeth, grooves or another surface configuration adapted to engage and hold the bone. Further, the surface may include bone ingrowth features to allow bone to penetrate the surface of the plate.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

It is understood that all spatial references, such as "horizontal," "vertical," "top," "inner," "outer," "bottom," "left," "right," "anterior," "posterior," "superior," "inferior,"

"medial," "lateral," "upper," and "lower" are for illustrative purposes only and can be varied within the scope of the disclosure. In the claims, means-plus-function clauses are intended to cover the elements described herein as performing the recited function and not only structural equivalents, but also equivalent elements.

I claim:

1. A fixation system for fixedly joining at least two spinous processes of a spinal column, the system comprising:
a first elongated plate extending generally along a first longitudinal axis having a substantially planar medial bone facing surface and a substantially planar lateral facing surface disposed opposite the bone facing surface, a channel extending along a majority of a length of the bone facing surface, a bone growth promoting material disposed within the channel, and a retention member extending over the channel to retain the bone growth promoting material within the channel, at least one opening extending through the first elongated plate substantially transverse to the first longitudinal axis;
a second elongated plate extending generally along a second longitudinal axis having a medial bone facing surface and a lateral facing surface disposed opposite the bone facing surface, a channel extending along a majority of a length of the bone facing surface, a bone growth promoting material disposed within the channel, and a retention member extending over the channel to retain the bone growth promoting material within the channel, at least one opening extending through the second elongated plate substantially transverse to the second longitudinal axis; and
at least one fastener sized and shaped to extend through the at least one opening of the first elongated plate and through the at least one opening of the second elongated plate to connect the first elongated plate to the second elongated plate;
wherein the channels of the first and second elongated plates are each defined by a planar inner surface extending substantially parallel to the substantially planar medial bone facing surface and an inner wall extending around the planar inner surface between the substantially planar medial bone facing surface and the planar inner surface, the inner wall having a generally cylindrical profile;
wherein the bone facing surface of the first elongated plate includes a first plurality of bone-engaging protrusions surrounding the channel, the first plurality of bone engaging protrusions extending through the mesh retention member;
wherein the bone facing surface of the second elongated plate includes a second plurality of bone-engaging protrusions surrounding the channel, the second plurality of bone engaging protrusions extending through the mesh retention member;
wherein the first elongated plate has a first thickness between the medial bone facing surface and the lateral facing surface, and the channel of the first elongated plate has a first depth from the medial bone facing surface to the planar inner surface that is greater than 50% of the first thickness; and
wherein the second elongated plate has a second thickness between the medial bone facing surface and the lateral facing surface, and the channel of the second elongated plate has a second depth from the medial bone facing surface to the planar inner surface that is greater than 50% of the second thickness.

2. The fixation system of claim 1, wherein the first and second plates are curved along their lengths to substantially match a curvature of the spinal column.

3. The fixation system of claim 1, wherein the at least one fastener comprises:
an elongated bolt comprising a proximal portion and a distal portion, the proximal portion comprising a head and the distal portion comprising a threaded post;
a first nut for threadingly mating with the threaded post of the elongated bolt.

4. The fixation system of claim 3, wherein the at least one fastener further comprises a second nut for threadingly mating with the threaded post to prevent loosening of the first nut.

5. The fixation system of claim 1, wherein the first elongated plate comprises at least two openings extending through the first elongated plate substantially transverse to the first longitudinal axis, wherein the second elongated plate comprises at least two openings extending through the second elongated plate substantially transverse to the second longitudinal axis.

6. The fixation system of claim 5, further comprising at least two fasteners each sized and shaped to extend through the at least two openings of the first elongated plate and through the at least two openings of the second elongated plate to connect the first elongated plate to the second elongated plate.

7. The fixation system of claim 5, wherein the at least two openings of the first and second elongated plates are spaced from one another, such that when the first and second elongated plates are positioned adjacent to a first spinous process of the at least two spinous processes at least one of the openings is positioned above the first spinous process and at least one of the openings is positioned below the first spinous process.

8. The fixation system of claim 1, wherein retention member extending over the channel of the first elongated plate comprises a mesh structure having a pore size between 50 microns and 1000 microns.

9. A fixation plate system for joining at least two spinous processes of a spinal column, the system comprising:
a first elongated plate sized and shaped for positioning along a first side of the at least two spinous processes, the first elongated plate extending generally along a first longitudinal axis and comprising a medial bone facing surface, a lateral facing surface disposed opposite the bone facing surface, a first side surface extending between the medial bone facing surface and the lateral facing surface, a second side surface extending between the medial bone facing surface and the lateral facing surface opposite the first side surface, a first end surface extending between the medial bone facing surface, the lateral facing surface, the first side surface, and the second side surface, and a second end surface extending between the medial bone facing surface, the lateral facing surface, the first side surface, and the second side surface opposite the first end surface, a channel extending along the bone facing surface, a bone growth promoting material disposed within the channel, a mesh retention member extending over the channel to retain the bone growth promoting material within the channel, and a plurality of bone-engaging protrusions extending through the mesh retention member and surrounding the channel;
a second elongated plate sized and shaped for positioning along a second side of the at least two spinous processes opposite the first side of the at least two spinous processes, the second elongated plate extending generally along a second longitudinal axis and comprising a medial bone facing surface and a lateral facing surface disposed opposite the bone facing surface, and at least one fastener sized and shaped to fixedly connect the first elongated plate to the second elongated plate when the first and second plates are positioned along the first and second sides of the at least two spinous processes;

wherein the channel of the first elongated plate is defined by an inner surface extending generally parallel to the medial bone facing surface and an inner wall extending around the inner surface between the substantially medial bone facing surface and the inner surface, the inner wall having a first inner side surface, a second inner side surface opposite the first inner side surface, a first inner end surface extending between the first and second inner side surfaces, and a second inner end surface extending between the first and second inner side surfaces opposite the first inner end surface;

wherein the first elongated plate has a first thickness between the medial bone facing surface and the lateral facing surface, and the channel of the first elongated plate has a first depth from the medial bone facing surface to the inner surface that is greater than 50% of the first thickness;

wherein the first elongated plate has a first width between the first side surface and the second side surface, and the channel has a second width extending between the first inner side surface and the second inner side surface, the second width being approximately 50% of the first width.

10. The fixation plate of claim 9, wherein at least the first elongated plate is curved along its length in a first direction to substantially match a curvature of the spinal column.

11. The fixation plate system of claim 9, wherein first elongated plate comprises at least one opening extending through the first elongated plate substantially transverse to the first longitudinal axis, and wherein the second elongated plate comprises at least one opening extending through the second elongated plate substantially transverse to the second longitudinal axis.

12. The fixation plate system of claim 11, wherein the at least one fastener comprises:

an elongated bolt comprising a proximal portion and a distal portion, the proximal portion comprising a head and the distal portion comprising a threaded post;

at least one nut for threadingly mating with the threaded post of the elongated bolt.

13. The fixation plate system of claim 9, wherein said bone growth promoting substance includes a carrier matrix in combination with a bone morphogenetic protein.

14. The fixation plate system of claim 13, wherein the mesh retention member comprises a pore size between 50 microns and 1000 microns.

15. The fixation plate system of claim 9, wherein the mesh retention member is removably joined to the first elongated plate.

16. The fixation plate system of claim 9, wherein the first elongated plate has a first thickness between the medial bone facing surface and the lateral facing surface, and the channel has a depth from the medial bone facing surface extending toward the lateral facing surface, the depth being greater than 50% of the first thickness.

17. The fixation plate system of claim 9, wherein the second elongated plate member further comprises a channel extending along the bone facing surface, a bone growth promoting material disposed within the channel, and a mesh retention member extending over the channel to retain the bone growth promoting material within the channel.

18. The fixation plate system of claim 9, wherein the mesh retention member comprises a pore size that allows bodily fluids to contact the bone growth promoting material through the mesh retention member.

19. A fixation system for fixedly joining at least two spinous processes of a spinal column, the system comprising:

a first elongated plate extending generally along a first longitudinal axis having a substantially planar medial bone facing surface and a lateral facing surface disposed opposite the bone facing surface, a continuous channel extending along a majority of a length of the bone facing surface, a bone growth promoting material disposed within the channel, a mesh retention member extending over the channel to retain the bone growth promoting material within the channel, and a first pair of openings extending through the first elongated plate substantially transverse to the first longitudinal axis;

a second elongated plate extending generally along a second longitudinal axis having a substantially planar medial bone facing surface and a lateral facing surface disposed opposite the bone facing surface, a continuous channel extending along a majority of a length of the bone facing surface, a bone growth promoting material disposed within the channel, a mesh retention member extending over the channel to retain the bone growth promoting material within the channel, and a second pair of openings extending through the second elongated plate substantially transverse to the second longitudinal axis;

a first fastener sized and shaped to extend through one of the first pair of openings of the first elongated plate and through one of the second pair of openings of the second elongated plate to connect the first elongated plate to the second elongated plate at a first position; and a second fastener sized and shaped to extend through one of the first pair of openings of the first elongated plate and through one of the second pair of openings of the second elongated plate to connect the first elongated plate to the second elongated plate at a second position;

wherein the first and second plates are curved along their lengths to substantially match a curvature of the spinal column;

wherein the continuous channels of the first and second elongated plates are each defined by a planar inner surface extending substantially parallel to the planar medial bone facing surface and an inner wall extending around the planar inner surface between and substantially perpendicular to the planar medial bone facing surface and the planar inner surface, the inner wall having a generally cylindrical profile;

wherein the first elongated plate has a first thickness between the medial bone facing surface and the lateral facing surface, and the channel of the first elongated plate has a first depth from the medial bone facing surface to the planar inner surface that is greater than 50% of the first thickness;

wherein the second elongated plate has a second thickness between the medial bone facing surface and the lateral facing surface, and the channel of the second elongated plate has a second depth from the medial bone facing surface to the planar inner surface that is greater than 50% of the second thickness; and wherein each of the first and second plates include a plurality of bone engaging protrusions extending from the medial bone facing surface and around the continuous channel, the plurality of bone engaging protrusions extending through the mesh retention member.

* * * * *